(12) United States Patent
Guetlin et al.

(10) Patent No.: US 10,709,484 B2
(45) Date of Patent: *Jul. 14, 2020

(54) CONTROL INSTRUMENT

(71) Applicant: DEPUY SYNTHES PRODUCTS, INC., Raynham, MA (US)

(72) Inventors: Michael Guetlin, Pratteln (CH); Sarah Mueller, Miami, FL (US); Janick Stucki, Bern (CH)

(73) Assignee: DePuy Synthes Products, Inc., Raynham, MA (US)

( * ) Notice: Subject to any disclaimer, the term of this patent is extended or adjusted under 35 U.S.C. 154(b) by 127 days.

This patent is subject to a terminal disclaimer.

(21) Appl. No.: 15/972,084

(22) Filed: May 4, 2018

(65) Prior Publication Data
US 2018/0250037 A1   Sep. 6, 2018

Related U.S. Application Data

(63) Continuation of application No. 14/767,531, filed as application No. PCT/IB2013/051168 on Feb. 13, 2013, now Pat. No. 9,949,770.

(51) Int. Cl.
*A61B 17/70* (2006.01)
*A61B 17/17* (2006.01)
(Continued)

(52) U.S. Cl.
CPC ...... *A61B 17/7082* (2013.01); *A61B 17/1757* (2013.01); *A61B 17/1796* (2013.01); *A61B 17/7076* (2013.01); *A61B 17/848* (2013.01); *A61B 17/864* (2013.01); *A61B 17/8875* (2013.01); *A61B 17/8897* (2013.01)

(58) Field of Classification Search
CPC . A61B 17/8897; A61B 17/7085; A61B 17/17; A61B 17/8875; A61B 17/7082; A61B 17/66; A61B 17/8872; A61B 17/92; A61B 17/864; A61B 17/7076;
(Continued)

(56) References Cited

U.S. PATENT DOCUMENTS 3,975,032 A    8/1976   Bent
5,843,001 A *  12/1998  Goldenberg ......... A61B 10/025
                                                      600/567
(Continued)

FOREIGN PATENT DOCUMENTS

JP    63-100158    6/1988
JP    8-257135    10/1996
JP    2010-57900   3/2010

OTHER PUBLICATIONS

US translation of Japanese Office Action dated Nov. 8, 2016 for JP2015-557527.

*Primary Examiner* — Ellen C Hammond
*Assistant Examiner* — Tara Rose E Carter

(57) ABSTRACT

A control instrument 100 for a guidewire comprising a first component moveable from a first position, in which the guidewire can move axially relative to the first component, to a second position in which the guidewire is fixed relative to the first component and a second, rotatable, component, wherein rotation of the second component causes the first component to move axially, only when the first component is in its second position, thereby moving the guidewire move axially.

12 Claims, 4 Drawing Sheets

(51) Int. Cl.
*A61B 17/86* (2006.01)
*A61B 17/88* (2006.01)
*A61B 17/84* (2006.01)

(58) Field of Classification Search
CPC ... A61B 17/7091; A61B 17/848; A61B 17/86; A61B 50/20
See application file for complete search history.

(56) References Cited

U.S. PATENT DOCUMENTS

| | | | |
|---|---|---|---|
| 5,902,305 A | 5/1999 | Beger | |
| 6,405,733 B1* | 6/2002 | Fogarty | A61B 90/39 128/899 |
| 6,827,722 B1 | 12/2004 | Schoenefeld | |
| 7,081,122 B1* | 7/2006 | Reiley | A61B 17/34 606/185 |
| 7,207,995 B1* | 4/2007 | Vandewalle | A61B 17/8875 606/104 |
| 7,938,848 B2 | 5/2011 | Sweeney | |
| 8,267,873 B2 | 9/2012 | Yanuma | |
| 8,641,717 B2 | 2/2014 | Defossez | |
| 2005/0273090 A1 | 12/2005 | Nieman | |
| 2005/0288654 A1 | 12/2005 | Nieman | |
| 2006/0089661 A1 | 4/2006 | Dodge | |
| 2007/0161985 A1 | 11/2007 | Demakas | |
| 2007/0260184 A1* | 11/2007 | Justis | A61B 17/16 604/164.01 |
| 2009/0275954 A1 | 11/2009 | Phan | |
| 2011/0319946 A1 | 12/2011 | Levy | |
| 2012/0004665 A1* | 1/2012 | Defossez | A61B 17/8872 606/108 |

* cited by examiner

CONTROL INSTRUMENT

CROSS REFERENCE TO RELATED APPLICATION

This application is a continuation of and claims priority to U.S. application Ser. No. 14/767,531 filed Aug. 12, 2015, which is a National Stage 35 U.S.C. 371 of International Patent Application PCT/IB62013/051168 filed Feb. 13, 2013.

FIELD OF THE INVENTION

The present invention relates to a control instrument, in particular a control instrument for a screwdriver, having a control mechanism for a guidewire.

BACKGROUND OF THE INVENTION

The placement of screws in minimal invasive surgery pedicle screw systems is commonly done using cannulated screws. These cannulated screws are positioned by placing over K-Wire. They are then screwed into position in the bone. During the placement of the screws over the K-wire, the K-wire must not be pushed forward, in order to avoid protrusion of the K-wire through the vertebral body. To control the migration of the K-wire, the surgeon uses fluoroscopy. However, it is desired to be able to control the position of the K-wire as the screw is placed to ensure that it does not interfere with the insertion of the pedicle screw without input from the surgeon. Hence, it is desirable to provide a screw driver or adapt an existing screwdriver such that as the screw is inserted into the pedicle the position of the K-wire is controlled. U.S. Pat. No. 7,207,995 discloses a cannulated medical instrument for insertion of a medical device over a guidewire. The instrument includes a cannulated follower member. A clasping device is connected to the cannulated follower member and moves the guidewire distally away from the cannulated driver member at an extraction rate.

SUMMARY OF THE INVENTION

In a first illustrative embodiment there is provided a control instrument for a guidewire comprising a first component moveable from a first position, in which the guidewire can move axially relative to the first component, to a second position in which the guidewire is fixed relative to the first component and a second, rotatable, component, wherein rotation of the second component causes the first component to move axially only when the first component is in its second position, thereby moving the guidewire axially.

In this way, the position of the guidewire is controlled. It can be held in or removed from its initial placement depending on the rate of movement of the first component relative to the second. Since the first component can only move when it is in its second position, it is ensured that the first component cannot move axially without the guidewire being fixed relative to it so that the guidewire is also moved axially.

Preferably a screw-engaging portion is connected to the second component such that the screw-engaging portion rotates as the second component rotates.

Since the second component is connected to the screw-engaging portion, rotation of the second component inserts the screw. Thus, the position of the guidewire is controlled as the screw is inserted.

Preferably the screw-engaging portion is connectable to a standard pedicle screw.

This means that the device can be used to insert pedicle screw systems without requiring modification to the screw system.

Preferably, the control instrument comprises a handle which rotates the second component.

This affords the user with a practical way of manipulating the second component to rotate the screw-engaging portion.

Preferably the control instrument comprises a releasable locking mechanism between the second component and the handle such that the second component can only rotate when the first component is in the second position.

Advantageously, the releasable locking mechanism ensures that the second component cannot be rotated until the first component is in its second position, i.e. the second component cannot rotate, and thus cause insertion of a screw until the first component is gripping the guidewire.

Preferably the releasable locking mechanism comprises a protrusion on one of the second component and the handle and a corresponding recess on the other of the second component and the handle, wherein the protrusion engages the recess when the first component is in the second position.

The protrusion and recess offer a secure connection between the second component and the handle.

The control instrument may comprise a wedge which moves the protrusion and recess into engagement such that they are locked in rotation.

The wedge acts to provide a levered force to move the locking mechanism into position.

The control instrument may comprise a grip which moves the first component into engagement with the guidewire.

The grip makes it easier for the user to move the device into the second position.

The grip may comprise two semi-cylindrical components which move radially relative to the guidewire.

This configuration provides the user with a more ergonomic device.

The grip may be resiliently biased into the first position.

In this way, accidental compression of the handles can be avoided.

Preferably, the first component comprises at least one gripping member which fixedly engages the guidewire.

The first component may comprise two gripping members which, in the second position, approach one another about the guidewire.

The two gripping members provide a secure means for holding the guidewire fixed relative to them.

The at least one gripping member may engage a thread and be rotated with the second component to cause axial movement.

This provides an elegant mechanical way of moving the first component and guidewire axially as the second component is rotated.

The thread may be positioned on an inner surface of at least one handle.

This ensures that the first component can only move axially when the handle is engaged with the first component.

A third illustrative embodiment provides for use of a screw driver as described above in a method of screwing pedicle screws to bone.

DETAILED DESCRIPTION OF THE DRAWINGS

Figure 1:
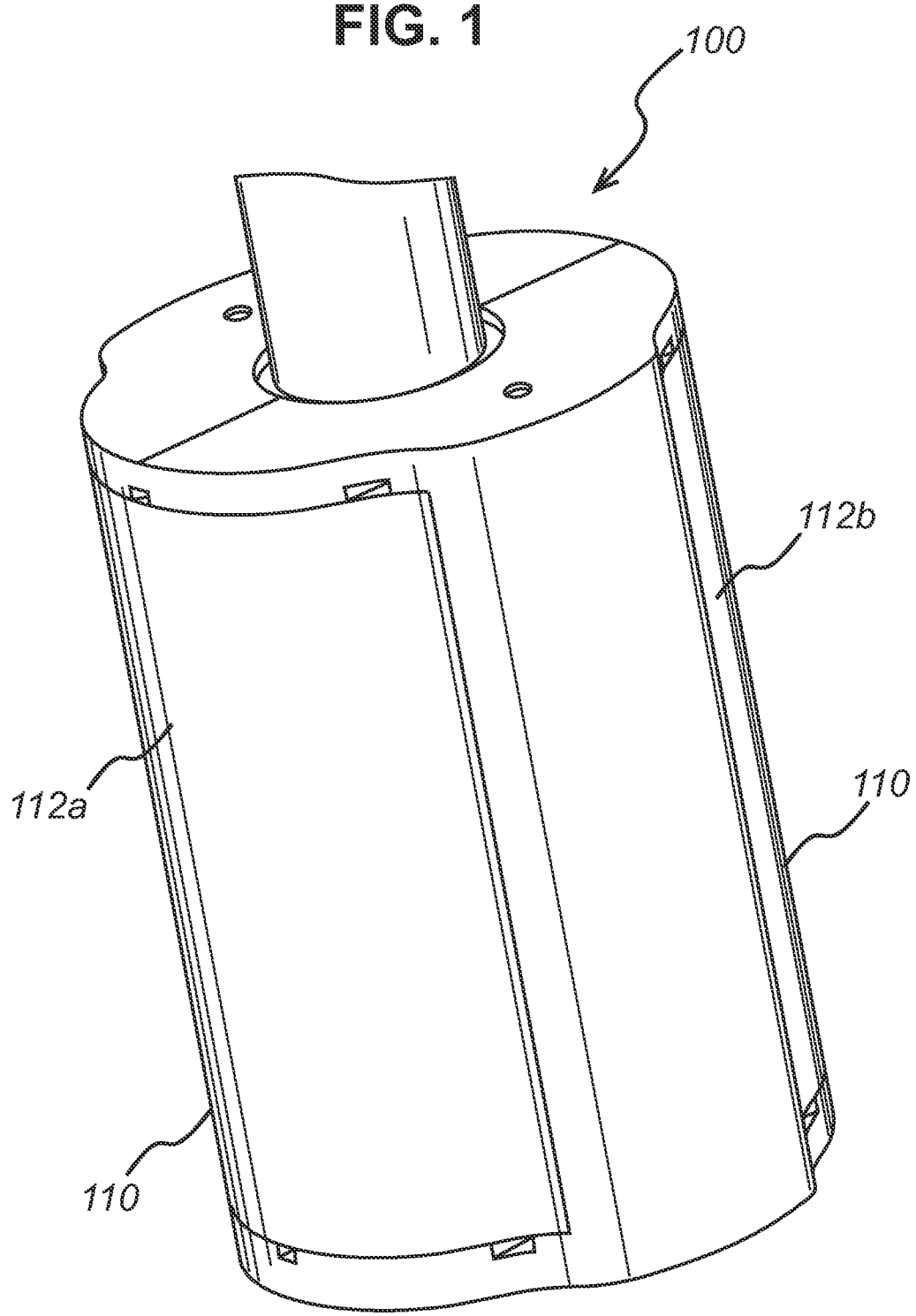
FIG. 1 shows a perspective view of a control instrument.

FIG. 1 shows a control instrument 100 for a screwdriver. The control instrument has a handle 110. The handle 110 is formed of two semi cylindrical components 112a, 112b and surrounds an aperture 200 (shown in FIG. 2) in the body of the device though which a K-wire can be passed. The handle 110 is moveable from a first position (as shown in FIGS. 1 and 2) to a second position (shown in FIGS. 3a and 3b), and is preferably resiliently biased into the first position.

Figure 2:
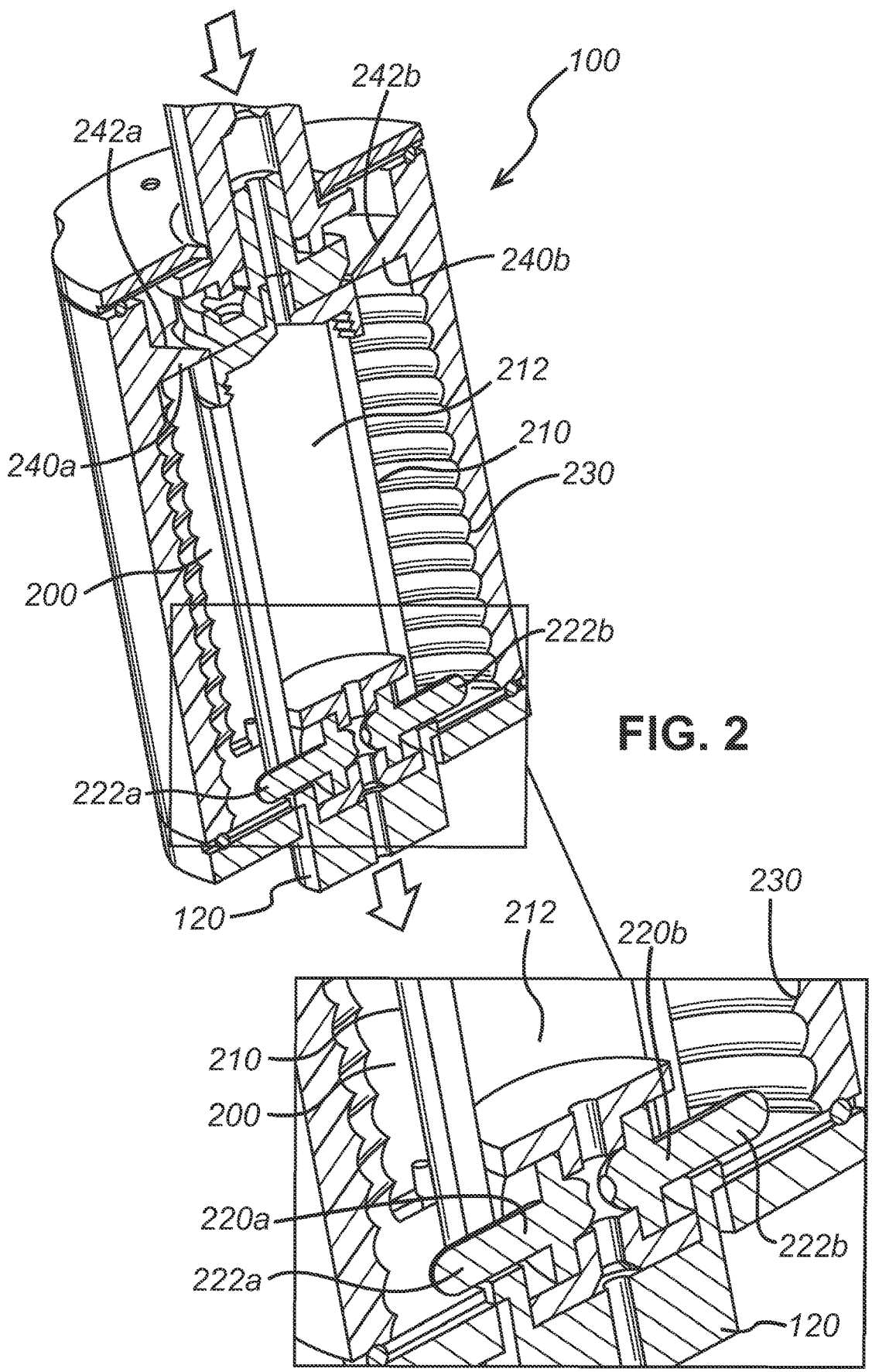
FIG. 2 shows a cross-section of a device, as described hereinafter, in a first position.

As shown in FIG. 2, positioned within the aperture 200 of the device is an additional cylindrical component 210, having an aperture 212 extending therethrough. In use, the K-wire passes through the aperture 212 of the cylindrical component 210. The cylindrical component 210 extends from a screw-engaging portion 120 of the device which protrudes from the device at a first end, and rotates therewith. The screw-engaging portion may engage a screw directly or may be connected to an existing screw driver. Positioned within the cylindrical component 210 are two gripping members 220a, 220b which are moveable between a first position, in which they allow passage of a K-wire therethrough, and a second position in which they are able to grip the K-wire. The gripping members 220a, 220b, are positioned within a guide 250 disposed within the cylindrical component 210. As can be seen in FIG. 2, the internal diameter of the semi cylindrical components 112a, 112b comprises a thread 230. The gripping members 220a, 220b have extensions 222a, 222b which extend outside the cylindrical component 210 and are engageable with the thread 230, when the semi cylindrical components 112a, 112b are moved into their second position, as shown in FIG. 3a.

The control instrument 100 further includes comprises a T-handle (not shown) positioned at an end opposite the screw-engaging portion 120. The T-handle engages the cylindrical component 210 of the screw driver 100 to rotate it and thus the screw-engaging portion 120. The T-handle comprises protrusions 310a, 310b. The control instrument 100 further includes a locking component 320. The locking component 320 is rotatably connected to the cylindrical component 210 and has apertures 322a, 322b which correspond to the protrusions 310a, 310b on the T-handle. The locking component 320 is moveable along the axis of the device in a direction shown by arrow A from a first position, in which the apertures 322a, 322b are disengaged from the protrusions 310a, 310b on the T-handle and a second position in which the apertures 322a, 322b engage the protrusions 310a, 310b on the T-handle. In this second position, the T-handle is rotatably connected, via the locking component 320, to the cylindrical component 210 and hence to the screw-engaging portion 120.

The handle 110 further comprises projections 240a, 240b on its inner diameter, as shown in FIG. 2. The projections 240a, 240b are positioned at an end of the handle 110 opposite the screw-engaging portion 120 of the device. The projections 240a, 240b include sloped surfaces 242a, 242b which engage with camming surfaces of the locking component 320 such that when the handle 110 is moved into its second position, the projections 240a, 240b act on the locking component 320, moving it axially in the direction of arrow A into its second position.

Figure 3A:
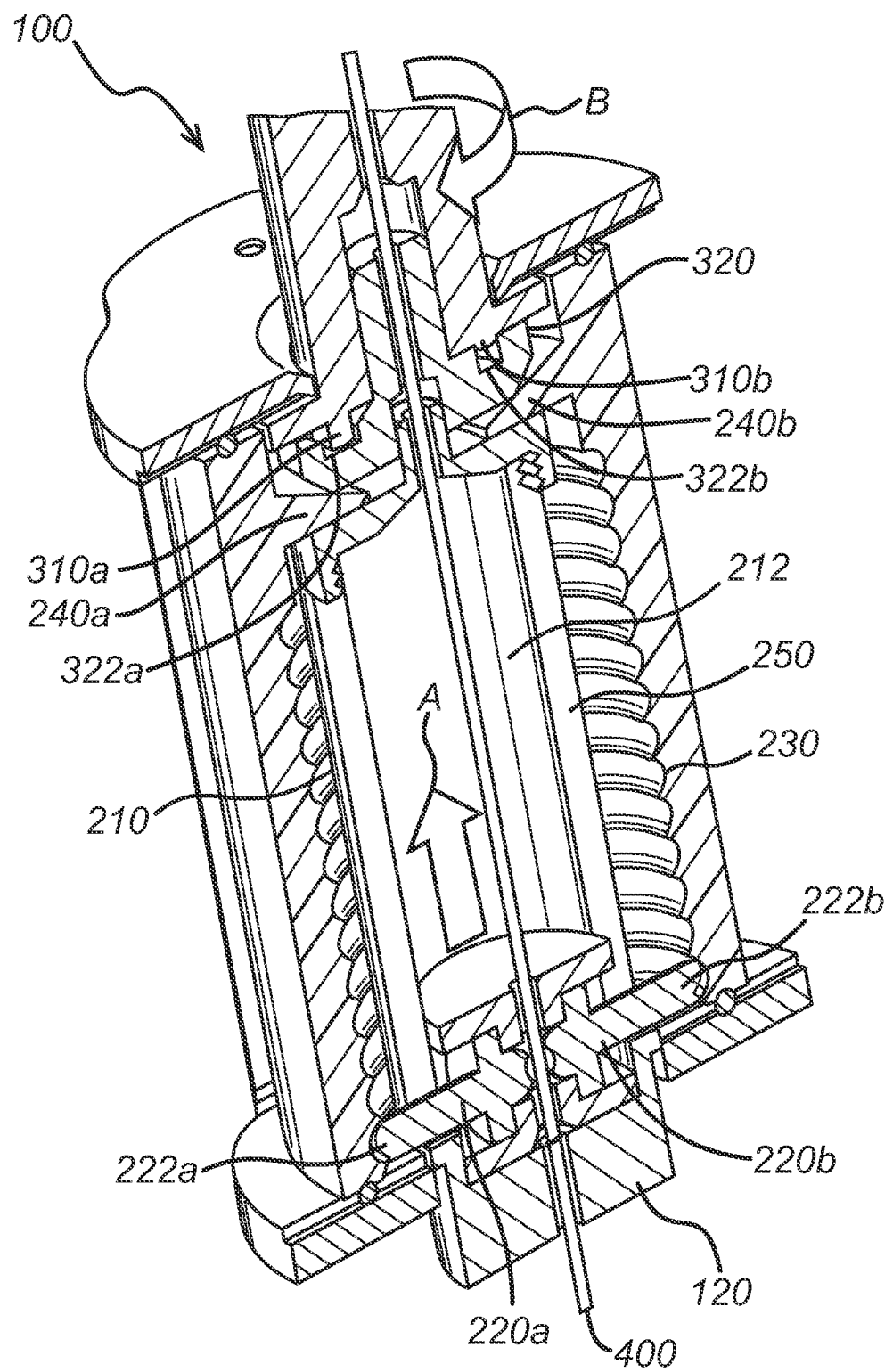
FIG. 3a shows a cross-section of a device, as described hereinafter, in a second position.
Figure 3B:
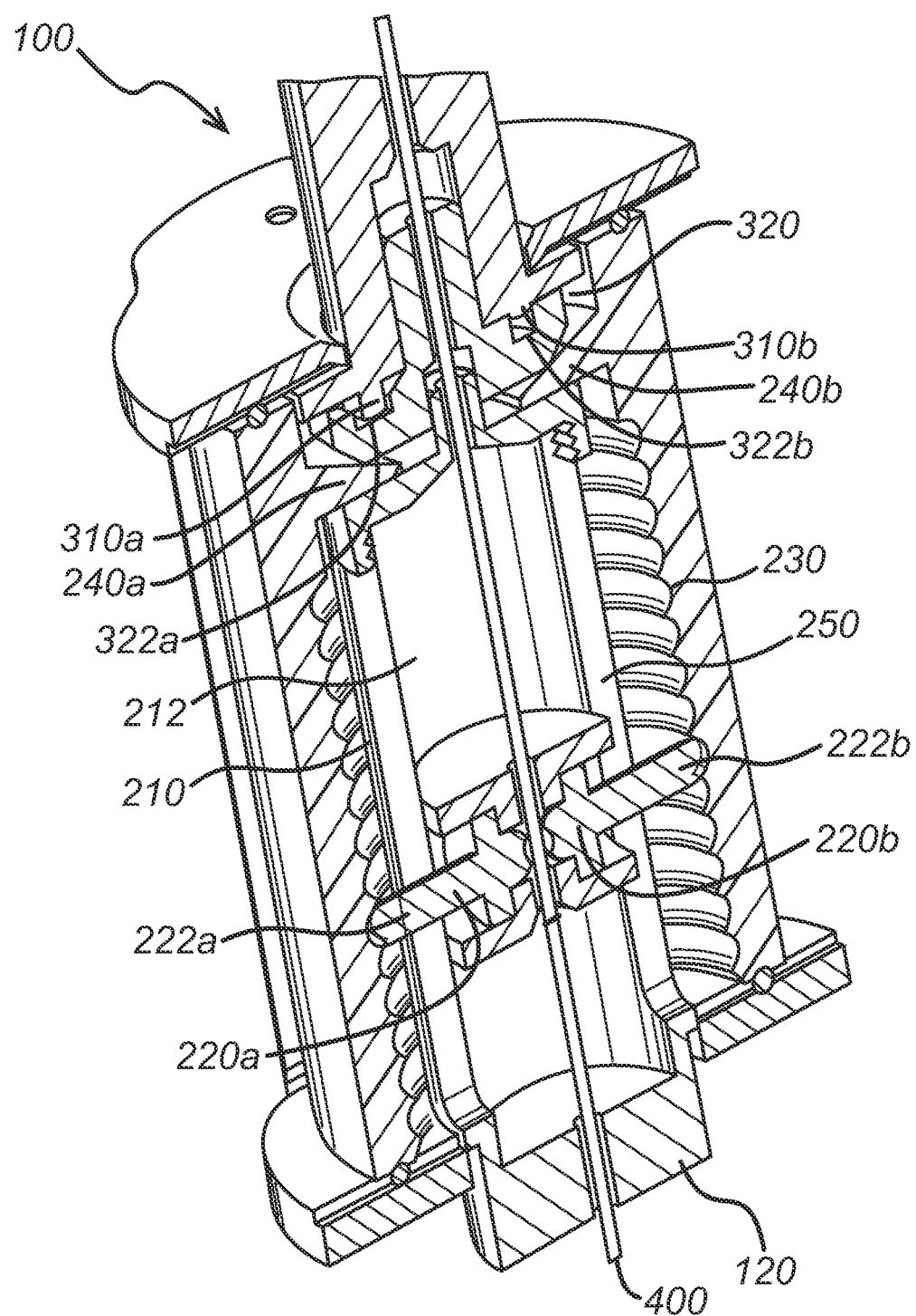
FIG. 3b shows a cross-section of a device, as described hereinafter, in a third position.

In use, as shown in FIGS. 3a and 3b, once the screw has been passed down the K-wire 400 and placed at the position into which it is to be inserted into the bone, the handle 110 is compressed into its second position, thereby moving the gripping members 220a, 220b into engagement with the K-wire 400 and moving the handle projections 240a, 240b into engagement with the locking component 320. The locking component 320 is moved in the direction of arrow A, by the projections 240a, 240b so that the protrusions 310a, 310b of the handle are inserted into the apertures 322a, 322b of the locking component 320. The T-handle is then rotatably engaged with the screw-engaging portion 120 as described above such that, as the T-handle is rotated in the direction shown by arrow B, the cylinder 210 and thus the screw engaging position 120 is rotated, screwing the pedicle screw into position. As the cylindrical component 120 is rotated, the gripping members 220a, 220b are also rotated and, by virtue of the thread 230 disposed on the interior of the handle 110, the gripping members 220a, 220b move in an axial direction towards the handle their movement directed by guide 250, along the direction of arrow A, thereby removing the K-wire 400 axially as the screw is inserted. Depending on the pitch of the screw thread in comparison to the pitch of the handle, as the cylindrical component is rotated the K-wire may be removed from its position or it may be retained in its initial position relative to the bone.

The control instrument may be an integral part of a screw driver or may be placed between the handle and screw-engaging portion of an existing instrument.

It will of course be understood that the present invention has been described above purely by way of example, and that modifications of detail can be made within the scope of the invention.

The invention claimed is:

1. A control instrument for a guidewire comprising:
a first component moveable from a first position, in which the guidewire can move axially relative to the first component, to a second position in which the guidewire is fixed relative to the first component;
a second, rotatable, component, wherein rotation of the second component causes the first component to move axially, only when the first component is in its second position, thereby moving the guidewire axially;
a handle which rotates the second component; and
a releasable locking mechanism between the second component and the handle such that the second component can only rotate when the first component is in the second position.

2. A control instrument according to claim 1, further comprising a screw-engaging portion connected to the second component such that the screw-engaging portion rotates as the second component rotates.

3. A control instrument according to claim 2, wherein the screw-engaging portion is connectable to a standard pedicle screw.

4. A control instrument according to claim 1, wherein the releasable locking mechanism comprises a protrusion on one of the second component and the handle and a corresponding recess on the other of the second component and the handle, wherein the protrusion engages the recess when the first component is in the second position.

5. A control instrument according to claim 4 further comprising a wedge which moves the protrusion and recess into engagement such that they are locked in rotation.

6. A control instrument according to claim 1, further comprising a grip which moves the first component into engagement with the guidewire.

7. A control instrument according to claim 6, wherein the grip comprises two semi-cylindrical components which move radially relative to the guidewire.

8. A control instrument according to claim 7, wherein the grip is resiliently biased into the first position.

9. A control instrument according to claim 1, wherein the first component comprises at least one gripping member which fixedly engages the guidewire.

10. A control instrument according to claim 9, wherein the first component comprises two gripping members which, in the second position, approach one another about the guidewire.

11. A control instrument according to claim 9, wherein the at least one gripping member engages a thread and is rotated with the second component to cause axial movement.

12. A control instrument according to claim 11, wherein the thread is positioned on an inner surface of a handle.

* * * * *